United States Patent [19]
Aoki et al.

[11] Patent Number: 4,829,179
[45] Date of Patent: May 9, 1989

[54] SURFACE ANALYZER

[75] Inventors: Masahiko Aoki; Masashi Konishi; Yasuhiro Matsuda; Naoto Okazaki, all of Kyoto, Japan

[73] Assignee: Nissin Electric Company, Limited, Kyoto, Japan

[21] Appl. No.: 70,252

[22] Filed: Jul. 6, 1987

[30] Foreign Application Priority Data

Jul. 12, 1986 [JP] Japan ................. 61-164299
Oct. 1, 1986 [JP] Japan ................. 61-235397
Dec. 16, 1986 [JP] Japan ................. 61-299269

[51] Int. Cl.$^4$ ............................ G01N 23/00
[52] U.S. Cl. ..................... 250/309; 250/296; 250/297
[58] Field of Search ............ 250/298, 296, 299, 297, 250/309, 292, 306

[56] References Cited

U.S. PATENT DOCUMENTS

| | | | |
|---|---|---|---|
| 3,240,931 | 3/1966 | Wiley et al. | 250/299 |
| 3,617,739 | 11/1971 | Liebl | 250/298 |
| 3,812,354 | 5/1974 | Walter | 250/299 |
| 3,819,941 | 6/1974 | Carrico | 250/309 |
| 3,866,042 | 2/1975 | Vastel | 250/296 |
| 3,955,084 | 5/1976 | Giffen | 250/299 |
| 4,132,892 | 1/1979 | Wittmack | 250/292 |
| 4,564,758 | 1/1986 | Slodzian et al. | 250/309 |
| 4,694,170 | 9/1987 | Slodzian et al. | 250/309 |

Primary Examiner—Bruce C. Anderson
Assistant Examiner—Michael Aronoff
Attorney, Agent, or Firm—Finnegan, Henderson, Farabow, Garrett & Dunner

[57] ABSTRACT

A surface analyzer for analyzing physical properties of the surface of a sample by means of PELS (Proton energy loss spectroscopy) in which accelerated ion beams such as proton beams impinge on the sample in the vertical direction to the surface of the sample and ion beams scattered from the sample are decelerated and then detected by an analyzer to analyze the energy loss of the ion beams. The surface analyzer comprises an ion beam source for generating ion beams, deflecting means for deflecting the ion beams from the ion beam source, irradiating the surface of the sample with the ion beams from the ion beam source in the vertical direction to the surface of the sample, and deflecting scattered ion beams from the sample, accelerating and decelerating means for accelerating the ion beams before the ion beams impinge on the sample and decelerating the scattered ion beams, and analyzing means for detecting the scattered beams and analyzing energy loss of the ion beams.

12 Claims, 10 Drawing Sheets

SURFACE ANALYZER

BACKGROUND OF THE INVENTION

1. Field of the Invention

The present invention relates to a surface analyzer that employs the technique of PELS (proton energy loss spectroscopy), in which a sample to be analyzed is irradiated by accelerated ion beams such as proton beams, and the beams scattered from the top few layers of the sample are decelerated by passage through a deceleration tube, and the energies of the decelerated scattered beams are measured to analyze physical properties of the surface of the sample.

2. Prior Art

A brief explanation of the basical principle of the PELS and a conventional surface analyzer employing PELS will be made hereinafter with reference to the accompanying drawings.

Suppose a proton of mass number m, moving with velocity U hits an atom of mass number M at rest at point O in FIG. 1. After collision, the proton glances off at velocity V along a path deflected from its original path by a scattering angle $\theta$ while the atom M recoils at velocity W in another direction at a scattering angle $\Phi$. Unlike electrons, the proton is heavy enough to impart motion to atom M and loses energy.

Since momentum is conserved in both x- and y-directions, the following two equations are established:

$$mU = mV\cos\theta + MW\cos\Phi \quad (1)$$

$$O = mV\sin\theta - MW\cos\Phi \quad (2)$$

If the collision is completely elastic, kinetic energy is conserved so that:

$$\tfrac{1}{2}mU^2 = \tfrac{1}{2}mV^2 + \tfrac{1}{2}MW^2 \quad (3)$$

Eliminating W from Eqs. (1) to (3), $$(\Gamma + 1)V^2 - 2U\cos\theta V - (\Gamma - 1)U^2 = 0 \quad (4)$$

$$\text{Then, } V = \frac{\cos\theta \pm \sqrt{\Gamma^2 - \sin^2\theta}}{\Gamma + 1} U \quad (5)$$

The plus sign in Eq. (5) indicated scattering at angle $\theta$ and the minus sign indicates scattering in opposite direction. Since this direction is attained by subtracting $\theta$ from $\pi$, only the plus sign should be taken in Eq. (5). It should also be noted that in Eq. (5) $\Gamma$ is defined as follows:

$$\Gamma = \frac{M}{m} \quad (6)$$

If the kinetic energy of the proton before collision is written as $E_0$, $$E_0 = \tfrac{1}{2}mU^2 \quad (7)$$

After collision, the kinetic energy of the proton is reduced to Ea. If the coefficient of attenuation K is defined as:

$$Ea = KE_0 \quad (8)$$

the following equation is obtained:

$$K = \frac{(\cos\theta \pm \sqrt{\Gamma^2 - \sin^2\theta})^2}{(\Gamma + 1)^2} \quad (9)$$

Eq. (9) is the formula for the energy of a proton scattered at angle $\theta$. This energy is dependent on $\theta$ but only to a small extent. In other words, Ea need not be measured for all values of $\theta$ and it suffices to measure Ea for a single value of $\theta$ after scattering of the proton. The atom with which the proton has collided can be specified by the parameter $\Gamma$. In Eq. (9), $\theta$ is not a variable but fixed.

A scattered proton at angle $\theta$ then enters an analyzer in which a voltage $V_0$ is applied between two parallel plates. A proton entering the analyzer through a slit will travel along a parabolic path and fall into either one of the channels in a micro channel plate.

The distance, L, from the slit and the falling position of the proton is increased as the energy of the proton increases. In other words, the energy of a proton Ea can be determined by measuring L.

If the charge on a proton is written as ze, the proton in the space of the analyzer will receive a force $zeV_0/h$ in a direction perpendicular to the plates which are spaced apart by h.

The velocity of the proton travelling through the analyzer is divided into two components, one being longitudinal and the other being transversal (i.e., perpendicular to the plates). The speed of the longitudinal component u is constant and that of the transversal component v varies. The proton passing through the slit will form a constant angle $\Psi$ with the surface of the nearer plate. The three parameters, u, v and $\Psi$, can be correlated by the following equations:

$$u = \left(\frac{2Ea}{m}\right)^{1/2} \cos\Psi \quad (26)$$

$$v = \left(\frac{2Ea}{m}\right)^{1/2} \cos\Psi - \frac{zeV_0 t}{h} \quad (27)$$

These kinetic equations are equivalent to those expressing the motion of an object thrown outwards under gravity.

From Eqs. (26) and (27), the distance L over which the proton travels in the analyzer in a direction parallel to the plates can be calculated as:

$$L = \frac{2Eah\sin(2\Psi)}{mzeV_0} \quad (28)$$

The highest resolution is attained when $\Psi = 45°$. Eq. (28) shows that the distance L from the slit to the falling position of the proton is proportional to the energy of the proton Ea. Therefore, the distribution of Ea, or the energy of proton, can be determined based on measurement of L.

In FIG. 2 showing the general layout of a prior art surface analyzer that employs PELS, ion beams such as proton beams extracted from an ionization source 2 are accelerated by an accelerating tube 6 and are optionally converged by a converging unit 8. Subsequently, the beams are deflected by a magnet for mass separation. After deflection, the ion beams impinge on a sample (not shown) in a scattering chamber 14. In order to irradiate a selected area of the sample by the ion beams, a slit (not shown) with a diameter of about 1 mmΦ is provided on the beam line preceding the entrance of ion beams into the scattering chamber 14. If He and other elements are used as sources of ion beams, not only monovalent but also divalent ions may be scattered from the sample, thereby increasing the complexity of measurement, so in the actual operation protons that exist only in the form of monovalent are employed ions. In FIG. 2, the numeral 12 denotes a vacuum pump.

The ion beams impinging on the sample are scattered by the top few layers of the sample. The scattered beams generally have varying values of energy and in order to reduce this spread of energy, a slit (not shown) of about 2 mmΦ is provided on the transport line of the scattered beams. The scattered beams passing through this slit are decelerated by a decelerating tube 18 and their energy spectrum is analyzed with a measuring instrument 20.

The method for determining the potential of the decelerated ion beams is hereunder described by referring to both FIGS. 2 and 3. Suppose that the ion beams are extracted from the ionization source 2 at a voltage of Ve, that the extracted ion beams are accelerated in the accelerating tube 6 by a voltage of V, and that the scattering chamber 14 has a zero potential assuming that it is grounded. Then, the total acceleration voltage of the ion beams, Va, is equal to the sum of V and Ve. If a table 19 (insulated from the ground) for mounting the measuring instrument 20 has a potential of Vd that is equal to Va minus an offset voltage Vo (that is, if the deceleration voltage Vd of the decelerating tube 18 is equal to Va−Vo), the scattered beams that enter the measuring instrument 20 after deceleration have an energy of q×Vo (eV) (disregarding the energy loss that occurs when the beam hit the sample) where q is the unit charge on an ion, for example, a proton.

The accelerating energy of the ion beams by which the sample is to be irradiated is preferably high for various reasons among which the principal one is that highly energized ion beams have a low probability of neutralization. The ion beams typically have an accelerating energy of about 100 keV. On the other hand, the scattered beams preferably have a low energy for the purpose of achieving high-precision measurement of their energy spectra. In a typical case, the scattered ions are decelerated to less than about 1 keV.

Based on the measurement of the energy spectra of the thus decelerated scattered beams; the crystalline structure and other physical properties of the surface of a solid sample can be investigated. By referring to FIG. 4, if the ion beam 3 loses an energy of $\Delta E$ because of collision with the sample 15 and if the scattered beam 4 entering the measuring instrument 20 has an energy of E, then the following relationship holds good:

$$\Delta E = qVo - E \qquad (10)$$

because the energy E of the scattered beam 4 entering the measuring instrument 20 is expressed as:

$$E = qVa - \Delta E - q(Va - Vo) \qquad (11)$$

which can be rewritten as Eq. (10).

The measuring instrument 20 shown in FIG. 4 consists of an energy analyzer 21 and a detector 22 such as a channeltron. Writing $V_{ESA}$ for the voltage applied to the energy analyzer 21, the energy E can also be expressed as follows:

$$E = kqV_{ESA} \qquad (12)$$

where k is a constant.

As can be seen from Eqs. (10) and (12), the spectrum of energy loss can be determined by varying either the offset voltage Vo or the voltage $V_{ESA}$. Consider here the beams that are scattered by atoms in the top three monolayers of a sample; the beams scattered in the second and third top layers travel a longer distance in lattices than the beams scattered in the topmost layer and hence undergo more energy loss $\Delta E$, yielding a spectrum of the shape shown in FIG. 5.

In the conventional PELS equipment, the scattering angle $\theta$ (see FIG. 4) can only be set to a small angle, for example, below 10° for the following two reasons: as the scattering angle is increased from 0°, the solid angle $\theta$ of a scattered beam 4 is decreased to lower the efficiency of beam detection; secondly, if the scattering angle $\theta$ is too large, individual parts of the equipment will mechanically interfere with one another. However, if the scattering angle $\theta$ is below 10°, low scattering approach has the disadvantage that it is highly susceptible to the surface state of a sample to be analyzed and undergo "energy straggling" due to double scattering caused by the asperities on the sample, and energy spectra of the scattered beams become too broad to guarantee a very high precision of analysis.

If one wants to measure the origin of energy loss (i.e., the point at which a scattered beam 4 of $\Delta E = 0$ enters the measuring instrument 20) or the energy resolving power of the equipment by admitting the ion beams 3 directly into the instrument 20 without allowing them to be scattered by the sample 15, it is necessary to modify the connection of the beam transport line and other parts of the equipment subsequent to the scattering chamber 14 in such a manner that the scattering angle $\theta$ will be 0°. This reconnecting operation and subsequent jobs for achieving alignment are highly time-consuming. In addition, the reassembled equipment may not guarantee the same level of precision as achieved before.

Furthermore, Eq. (9) shows the in the neighborhood of $\theta \cong 0$, k does not vary with Γ, so that one value of Γ can not be easily distinguished from another.

SUMMARY OF THE INVENTION

As a result of their close studies conducted to know the relationship between the scattering angle $\theta$ and the solid angle of scattered beams 4, the present inventors found that by setting the scattering angle $\theta$ for a value of approximately 180°, a sharp energy spectrum could be obtained for scattered beams while achieving a significant improvement in the efficiency of beam detection.

Therefore, an object of the present invention is to provide a surface analyzer that is capable of not only easily obtaining a sharp energy spectrum for scattered beams and a high efficiency of beam detection but also the measurements of the origin of energy loss and the energy resolution, by setting a scattering angle to approximately 180°.

This object can be achieved by the surface analyzer of the present invention characterized by including a first deflecting magnet that deflects both an ion beam to impinge on a sample and a scattered beam from the sample and which is provided on the path of the two beams, and a second deflecting magnet that is provided on the path of a scattered beam passing through the first deflecting magnet and which deflects said scattered beam in the same direction as in the first deflecting magnet to be admitted into a decelerating tube, the analyzer being further characterized in that it satisfies the following conditions: $\Phi_1 = \Phi_2$, $\alpha_1 = \alpha_2 = (\Phi_1/2) - 90$ (degrees), and $r_1 = r_2$, where $\Phi_1$ is the angle of deflection of the scattered beam in the first deflecting magnet, $\alpha_1$ is the angle at which the scattered beam emerges from the first deflecting magnet, $r_1$ is the radius of curvature of a scattered beam with no energy loss in the first deflecting magnet, $\Phi_2$ is the angle of deflection of the scattered beam in the second deflecting magnet, $\alpha_2$ is the angle at which the scattered beam is admitted into the second deflecting magnet, and $r_2$ is the radius of curvature of a scattered beam with no energy loss in the second deflecting magnet.

Further, this object can be achieved by the surface analyzer of the present invention characterized by including a first deflecting magnet that deflects both an ion beam to impinge on a sample and a scattered beam from the sample and which is provided on the path of the two beams, and a second deflecting magnet that is provided on the path of a scattered beam passing through the first deflecting magnet and which deflects said scattered beam in the same direction as in the first deflecting magnet to be admitted into a measuring instrument, said analyzer being further characterized in that an accelerating/decelerating tube for not only accelerating the ion beams to be incident on the sample but also decelerating the scattered beams from the sample is provided between the first deflecting magnet and the sample.

Still further, this object can be achieved by the surface analyzer of this invention characterized by including a deflecting magnet provided on both a beam to impinge on the sample and scattered beams having various energy spectrum from the sample and deflecting the scattered beams in the parallel direction to one another on the same plane, and an analyzer, that has a broad position detector and an elongated slit, for detecting the parallel beams.

DETAILED DESCRIPTION OF THE INVENTION

Figure 20:
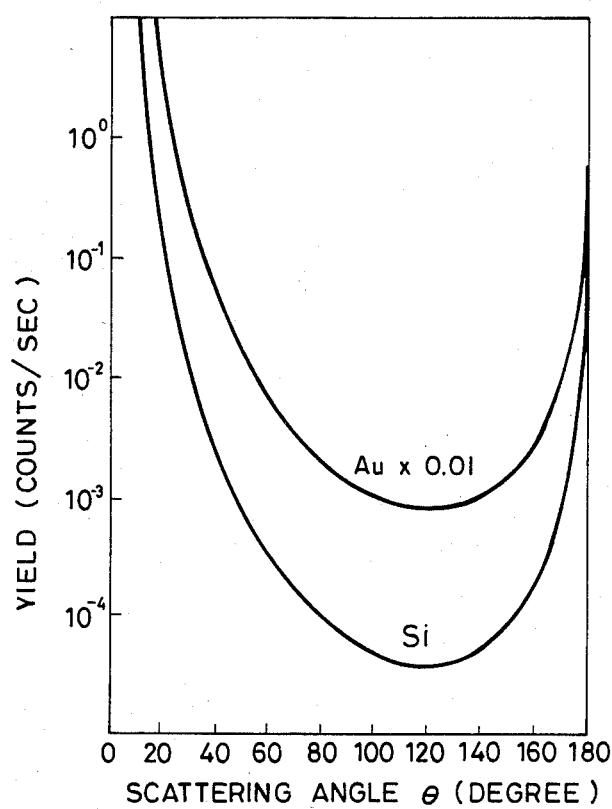
FIG. 20 is a graph showing the proton yield vs scattering angle for Au and Si.

As FIG. 20 shows, the scattering yield of ion beams such as protons is high in the vicinity of $\theta = 0°$ and $180°$. It therefore became evident that the neighborhood of $\theta = 180°$ would also be a promising region of scattering angle.

In addition, Eq. (9) shows that at $\theta = \pi$ (i.e., 180°) the $\Gamma$ dependency of K becomes strongest, so that the atom with which the proton has collided is more easily identified.

At $\theta = \pi$, the direction in which proton beams are incident on the sample coincides with their scattering direction so they must be separated by some means. To this end, the proton beams are bent by a deflecting magnet by 90° before they are incident on the sample, and the beams scattered in an anti-parallel direction are bent by 90° with another deflecting magnet before they are guided into a measuring system.

If $\theta = \pi$, K varies most pronouncedly with $\Gamma$ and the mass M of the atom with which the proton has collided can be determined in the least ambiguous manner.

Therefore, the following consideration is directed to the case where $\theta = \pi$. Eq. (9) can be rewritten as:

$$K = \left(\frac{\Gamma - 1}{\Gamma + 1}\right)^2 \tag{29}$$

The parameter $\Gamma$ denotes the ratio of the mass, M, of the atom with which the proton is to collide, to the mass, m, of the proton. The mass number of an atom is the mass of the atom with the atomic mass unit (1 amu = $1.6605655 \times 10^{-27}$ kg) being taken an unity. The mass of a proton, m, is $1.6726485 \times 10^{-27}$ kg. If the slight difference between the mass of the proton and the atomic mass unit is disregarded, $\Gamma$ is equal to the mass number of the atom of interest. Therefore, for the purposes of the following discussion, $\Gamma$ is referred to as mass number. The mass numbers so defined of several atoms are listed below together with corresponding K values:

O: $\Gamma = 16.00$, $K = 0.7785$
Al: $\Gamma = 26.98$, $K = 0.8621$
Si: $\Gamma = 28.085$, $K = 0.8672$
Ga: $\Gamma = 69.72$, $K = 0.94422$
As: $\Gamma = 74.9$, $K = 0.94799$
In: $\Gamma = 114.82$, $K = 0.9658$
Sb: $\Gamma = 121.7$, $K = 0.9677$
Pb: $\Gamma = 207.2$, $K = 0.98088$
Bi: $\Gamma = 208.98$, $K = 0.98104$.

In this way, the K values of all elements of atoms can be readily calculated.

Suppose the proton has an energy ($E_0$) of 100 keV before collision. After collision with Ga, it will have an energy ($E_1$) of 94.422 keV, and after collision with As, $E_1$ will be 94.799 keV. The difference between the two values of $E_1$ may be expressed by $\Delta E$ as follows:

$$\Delta E = 377 \text{ eV}$$

The proton will lose more energy if it is scattered by the lighter atom Ga and the differential energy loss is given by 377 eV. This is the theory that enables one to tell which of the two atoms, Ga and As, has caused the proton to scatter. In the case of Pb and Bi, $\Delta E = 16$ $eV$ and distinction between these two atoms can be made by using a detector having a resolving power of 5 eV.

Figure 6:
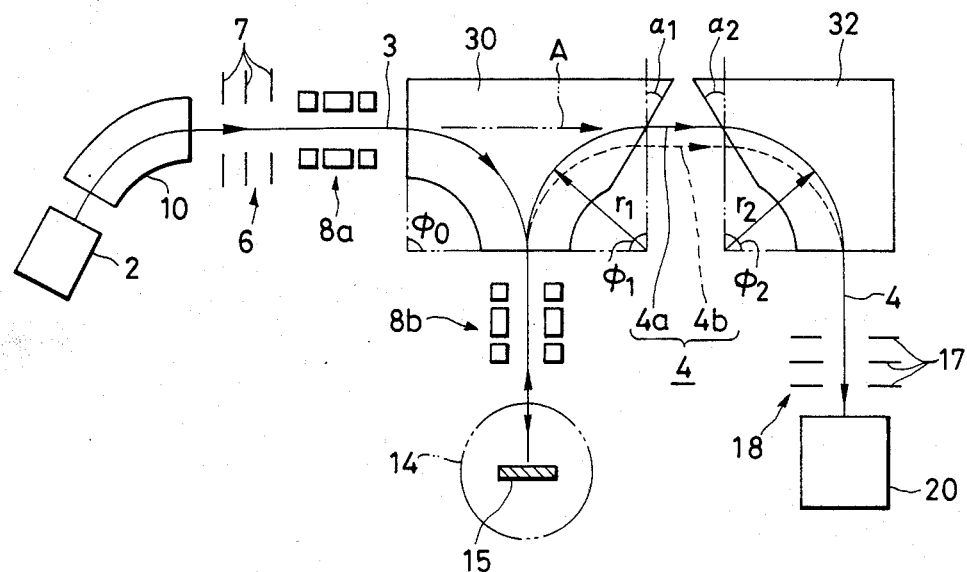
FIG. 6 is a schematic plan view of a surface analyzer according to first embodiment of the present invention.

FIG. 6 is a plan view showing the general layout of a surface analyzer according to first embodiment of the present invention. The operating principles of this analyzer are essentially the same as those of the above-described prior art system. Those components which do not have any particular relevance to the explanation of the differences from the prior art are omitted from FIG. 6.

In the apparatus shown in FIG. 6, a generally T-shaped first deflecting magnet 30 that is typically formed of an electromagnet is provided upstream of the scattering chamber 14. A unit for accelerating ion beams 3 and a unit for performing measurement on scattered beams 4 are provided upstream and downstream, respectively, of the magnet 30. This layout enables measurement for a scattering angle ($\theta$) of 180°.

Ion beams 3 such as proton beams that have been extracted from an ionization source 2 and which have been subjected to mass separation in a magnet 10 are introduced into an accelerating tube 6 that has a plurality of electrodes 7 and in which the beams are accelerated to an energy of about 100 keV as in the prior art. The accelerated beams are deflected by the deflecting magnet 30 on their path and admitted into the scattering chamber 14 (which may be held in an ultrahigh vacuum) to impinge on the sample 15. Since the sample 15 is mounted so as to provide a scattering angle ($\theta$) of 180°, the ion beams 3 are incident perpendicular to the surface of the sample 15 and scattered beams 4 from the sample 15 also emerge in a direction perpendicular to its surface.

As a result, the scattered beams 4 travel backward on the same path as that of the ion beams 3 and pass through the deflecting magnet 30 by which they are deflected in a direction that is opposite the direction of the deflection of the ion beams 3. This second deflection enables the track of the incident ion beams 3 before impinging on the sample 15 to be separated from the track of the scattered beams 4 from the sample 15. It is noted that the magnetic flux generated by the deflecting magnet 30 is directed away from the paper.

A Q lens (electrostatic triple quadrupole lens) 8a is provided downstream of the accelerating tube 6 and another Q lens 8b is provided upstream of the scattering chamber 14. The Q lens 8a (or 8b) serves to shape the ion beams 3 (or scattered beams 4) so that they will be free from any divergence, specifically the divergence directed into or away from the paper. These Q lenses are not indispensable to the present invention but are preferably used for achieving a greater accuracy in measurement.

A second deflecting magnet 32 is provided on the path of incoming scattered beams 4 that have passed through the magnet 30. This magnet 32 deflects the scattered beams 4 in the same direction as achieved by the magnet 30 and admit them at a point near the central axis of a decelerating tube 18 having a plurality of electrodes 17. Like the first deflecting magnet 30, the magnet 32 is typically formed of an electromagnet and the magnetic flux it generates is directed away from the paper.

The decelerating tube 18 retards the scattered beams 4 to such an extent that their energy will to no more than about 1 keV as in the prior art. The decelerated scattered beams 4 are introduced into a measuring instrument 20 that measures the energy spectrum of the beams.

In the present invention, the deflecting magnet 32 is employed for the following reason: depending on the energy loss $\Delta E$ caused by scattering in the sample 15, the scattered beams 4 coming through the magnet 30 have been diffused by this magnet 30 as shown schematically in FIG. 6 by 4a (beams of $\Delta E = 0$) and 4b (beams of $\Delta E \neq 0$); the diffused beams 4 are reconverged into a single track by the magnet 32 before they are admitted into the decelerating tube 18. If the diffused scattered beams 4 are immediately introduced into the decelerating tube 18, they will remain diffused or may be sometimes further diffused because of the lens effect of the tube 18; the beam transport efficiency of such diffused beams that are admitted into the measuring instrument 20 varies with their energy loss $\Delta E$, potentially causing such disadvantages as the drop in the reliability of measurements and the difficulty in accomplishing quantitative analyses.

In order to eliminate these problems, the side of the deflecting magnet 30 on which scattered beams 4 travel is constructed in a way that is substantially symmetrical with the deflecting magnet 32. Stated more specifically, the two deflecting magnets are designed to satisfy the following conditions:

$$\left. \begin{array}{l} \Phi_1 = \Phi_2 \\ \alpha_1 = \alpha_2 = (\Phi_1/2) - 90 \text{(degrees) and} \\ r_1 = r_2 \end{array} \right\} \quad (13)$$

where $\Phi_1$ is the angle of deflection of the scattered beams in the magnet 30, $\alpha_1$ is the angle at which the scattered beams emerge from the magnet 30, $r_1$ is the radius of curvature of a scattered beam 4a with no energy loss ($\Delta E=0$), $\Phi_2$ is the angle of deflection of the scattered beams in the magnet 32, $\alpha_2$ is the angle at which the scattered beams are admitted into the magnet 32, and $r_2$ is the radius of curvature of the scattered beam 4a. In the embodiment under discussion, $\Phi_1=\Phi_2=90°$ and $\alpha_1=\alpha_2=-45°$ (the minus sign is generally attached to $\alpha_1$ and $\alpha_2$ in the case shown in FIG. 6).

If the three conditions noted above are satisfied, the scattered beams 4a and 4b that have been separated from a single track in the deflecting magnet 30 will travel on parallel paths as they emerge from the magnet 30 and enter the deflecting magnet 32, in which they are deflected in a manner that is just opposite to the manner of deflection effected in the magnet 30 and are recombined into a single track before leaving the magnet 32.

As a consequence, the scattered beams 4, irrespective of any difference that exists in their energy loss $\Delta E$, are admitted into the decelerating tube 18 as they travel on a single central track, and are thereafter introduced into the measuring instrument 20. This eliminates the chance of variations of occurring in the yield of ion beams coming into the measuring instrument 20 on account of the change in their energy loss $\Delta E$, and thereby enables a wide range of energy losses to be measured with high accuracy. An attendant advantage of the embodiment described above is that it eliminates the need to compensate for the change in beam detection efficiency that is caused by offsetting of the track of the scattered beams 4.

Figure 7:
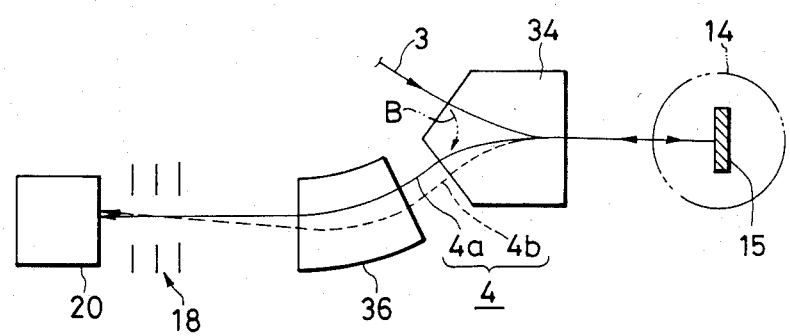
FIG. 7 is a schematic partial plan view of a surface analyzer according to second embodiment of the present invention.

FIG. 7 shows a plan view showing a second embodiment of the invention. A deflecting magnet 34 is used to separate the track of incident ion beams 3 from the track of scattered beams 4, thereby enabling measurement for a scattering angle ($\theta$) of 180°. The resulting dispersed beams 4 are then introduced into a deflecting magnet 36 that converges them at a point near the central axis of the decelerating tube 18 so as to eliminate the chance of variations of occurring in the yield of ion beams coming into the measuring instrument 20 on account of the change in their energy loss $\Delta E$. However, unlike the deflecting magnet 32 used in the first embodiment, the magnet 36 lacks a capability of converging the central tracks of scattered beams 4 of varying energy loss $\Delta E$ into a single track as they leave the magnet. Therefore, if the scatterd beams 4 of interest have suffered a broad range of energy loss $\Delta E$, the system according to the first embodiment will provide more accurate measurements than the system shown in FIG. 7.

Figure 5:
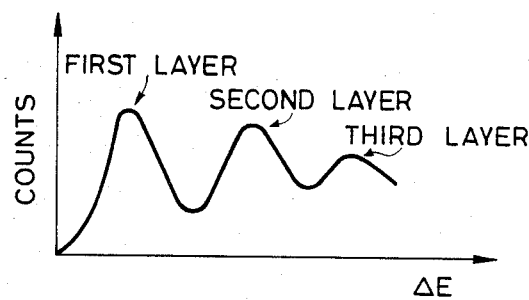
FIG. 5 shows an energy spectrum produced from the system shown in FIG. 2.
Figure 8:
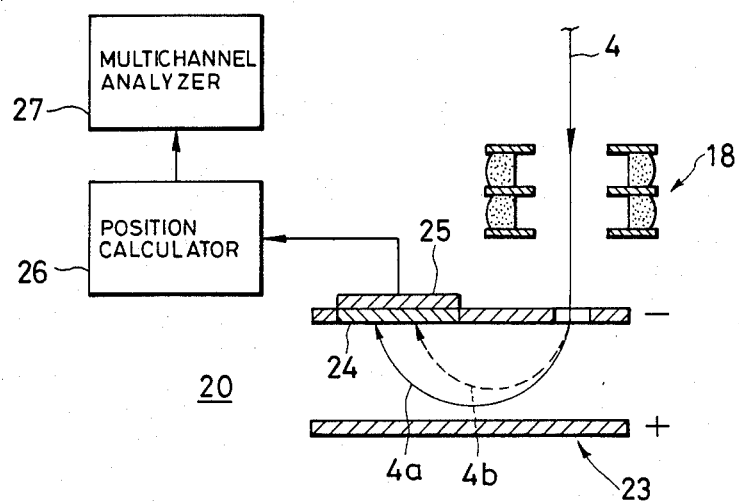
FIG. 8 is a schematic diagram of an example of the measuring instrument shown in FIG. 6.

An exemplary construction of the measuring instrument 20 is shown in FIG. 8 and this is effective for enabling a broad spectrum of energy to be measured at a time. As shown, the basic components of the instrument 20 are a parallel-plate analyzer 23, a micro-channel plate 24, and a position detector 25. The scattered beams 4 are dispersed at different points on the microchannel plate 24 according to their energies, or values of energy loss $\Delta E$, and the positions on which the beams have fallen are detected with the position detector 25 and a position calculator 26 which allows a multi-channel analyzer 27 to display the counts for the respective positions. Using this type of measuring instrument 20, the quantities of scattered beams form the top few layers of the sample 15 can be measured at a time by simply tilting the sample (the angle of its inclination depends both on the sample and on the specific monolayer in which the incident beams are to be scattered) and an energy spectrum of the shape shown in FIG. 5 can be attained with high efficiency without the need to change the offset voltage Vo or the voltage $V_{ESA}$ applied to the energy analyzer 21 as in the prior art. This offers the additional advantage of eliminating any of the effects that may be produced as a result of changes in the energy state occurring during the course of spectrum analysis.

Figure 9:
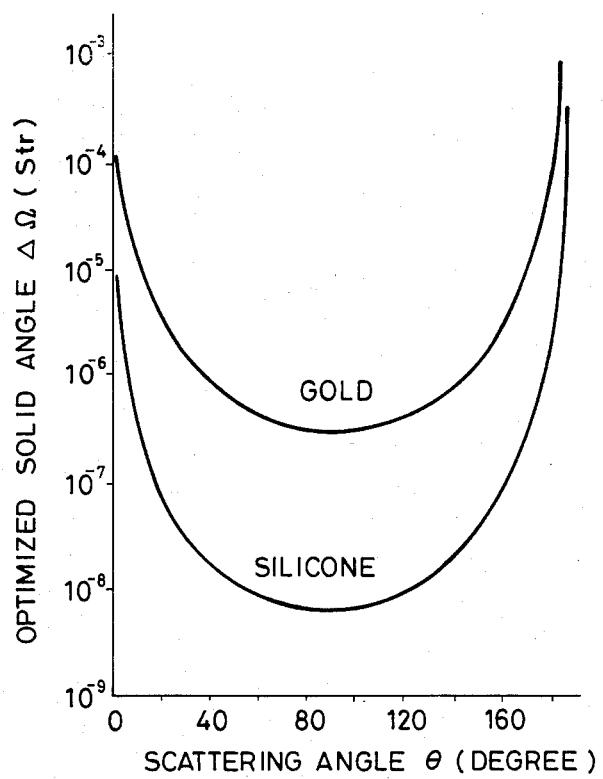
FIG. 9 is a graph showing the profile of optimized solid angle vs scattering angle.

FIG. 9 is a graph showing the profile of optimized solid angle vs scattering angle, the vertical axis being graduated on the logarithmic scale. As can be seen from FIG. 9, at $\theta=180°$ the optimized solid angle $\Delta\Omega$ (str), or the beam detection efficiency, is from several hundred (when the sample 15 is made of gold) to several thousand (when the sample 15 is made of silicon) times as high as when $\theta=20°$. In addition, at $\theta=180°$ the scattered beams 4 are insensitive to the surface asperities of the sample 15 and are only susceptible to the effects of atoms in the surface of the sample. Therefore, a sharp energy spectrum can be attained and a corresponding improvement is achieved in the precision of analysis.

If it is desired to measure the origin of energy loss or the energy resolving power of the equipment, one has only to control the polarity or flux density of the deflecting magnet 30 so that ion beams 3 admitted into that magnet are directly (i.e., without being impinged on the sample 15) permitted to emerge on the same track as that of the scattered beam 4a which has undergone no energy loss ($\Delta E=0$). This eliminates the existing need to modify the system layout and the problems associated with the prior art, such as the necessity for executing alignment jobs and other time-consuming operations and decreased precision of the reassembled equipment.

A particular advantage of the first embodiment shown in FIG. 6, in which $\Phi_1=\Phi_2=90°$ and $\Phi_0$ which is the angle of deflection of ion beams 3 in the magnet 30 is 90°, is that if one wants to measure the origin of energy loss or the energy resolving power of the equipment, all he has to do is to turn off the excitation of the magnet 30. If this is done, the ion beams 3 will go straight through the magnet 30 following the path indicated by A in FIG. 6 and will emerge from the magnet 30 to travel on the same track as that of the scattered beam 4a which has not suffered any energy loss ($\Delta E=0$). This provides great ease in accomplishing measurement of the origin of energy loss or the energy resolving power of the equipment.

In the apparatus shown in FIG. 7, by changing the polarity of the deflecting magnet 34 and increasing the flux density thereof, the ion beams 3 can be deflected by a large angle in the direction of B such as to enable measurement of the origin of energy loss or the energy resolving power of the apparatus. But according to the first embodiment shown in FIG. 6, the same purpose can be attained by simply turning off the excitation of the deflecting magnet 30.

As described above, the first and second embodiments achieve PELS with the scattering angle being set at a value of approximately 180° and this contributes to the yielding of a sharp energy spectrum while affording a significant improvement in beam detection efficiency. In addition, the scattered ion beams can be admitted into the decelerating tube with their central orbits being converged into a single track irrespective of the difference in their energy loss. This eliminates the variation in detection efficiency due to the difference in energy loss and thereby allows a broad range of energy to be measured in an accurate manner. As a further advantage, the present invention enables the origin of energy loss or the energy resolving power of equipment to be easily measured without changing the layout of the equipment.

Figure 10:
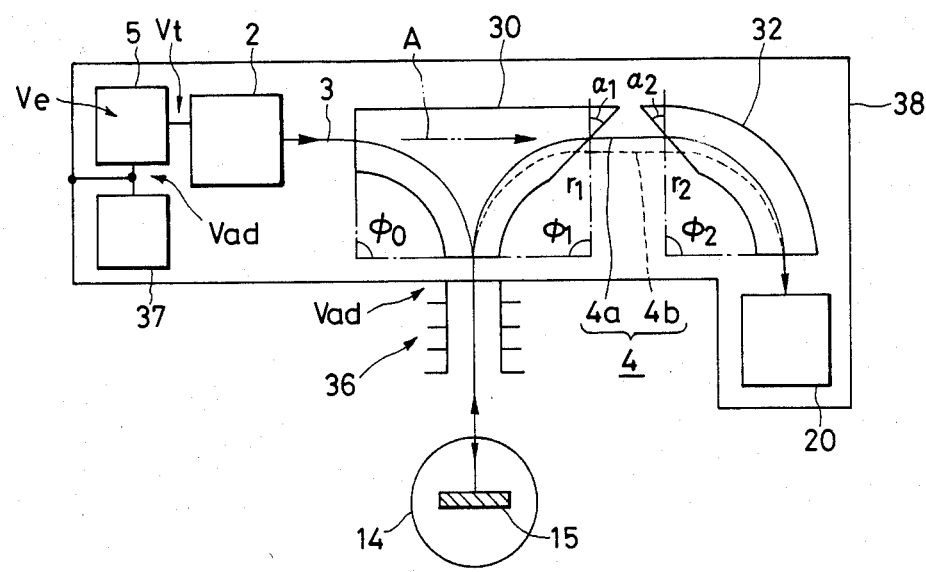
FIG. 10 is a schematic plan view of a surface analyzer according to third embodiment of the present invention.
Figure 12:
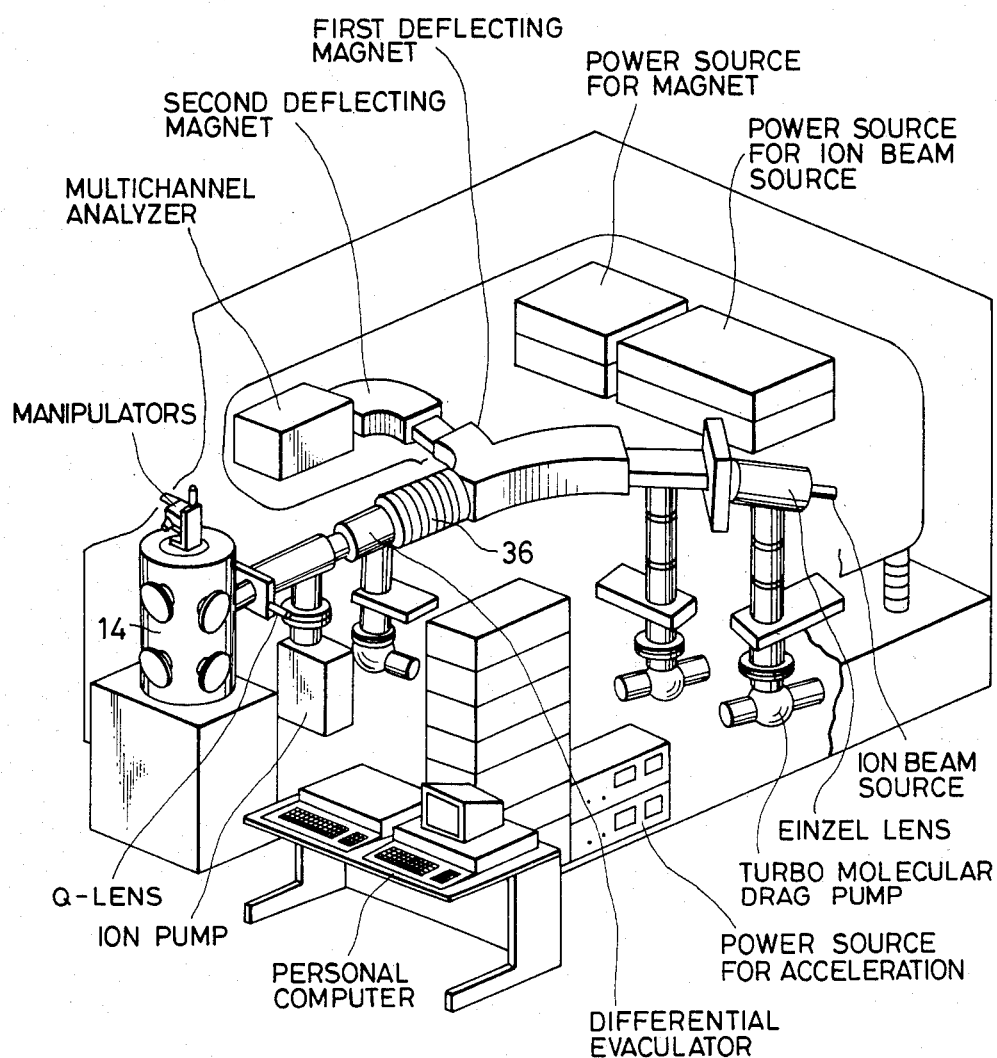
FIG. 12 is a perspective view showing the general layout of the third embodiment of the present invention.

FIGS. 10 and 12 are a schematic plan view and a perspective view of a surface analyzer according to the third embodiment of the present invention. The components which are identical or equivalent to those shown in FIG. 6 are identified by like numerals or omitted, and the following description is principally concerned with the differences between the two systems.

In the embodiment shown in FIG. 10, the accelerating tube 6 and the decelerating tube 18 shown in FIG. 6 are replaced by an accelerating/decelerating tube 36 that is provided between the first deflecting magnet 30 and the sample 15 in the scattering chamber 14 and which serves not only to accelerate the ion beams to be incident on the sample 15 but also to decelerate the scattered beams 4 from the sample 15. An accelerating-/decelerating voltage Vad is supplied to the tube 36 from a power source 37.

The ion beams 3 extracted from the ionization source 2 are first deflected in the deflecting magnet 30 by, for example, 90° and then accelerated in the tube 36. The accelerated beams are admitted into the scattering chamber 14 to impinge on the sample 15 which is mounted to provide a scattering angle $\theta$ of, say, 180°. The scattered beams 4 from the sample 15 travel in a direction opposite to that of the ion beams 3 and are admitted into the tube 36 in which they are decelerated. The decelerated beams are then introduced into the deflecting magnet 30 and deflected by, for example, 90° in a direction opposite to the deflection of the ion beams 3. The beams 4 are further deflected in the deflecting magnet 32 by, for example, 90° and then admitted into the measuring instrument 20. Numeral 5 represents a power source for supplying an extraction voltage Ve.

Figure 11:
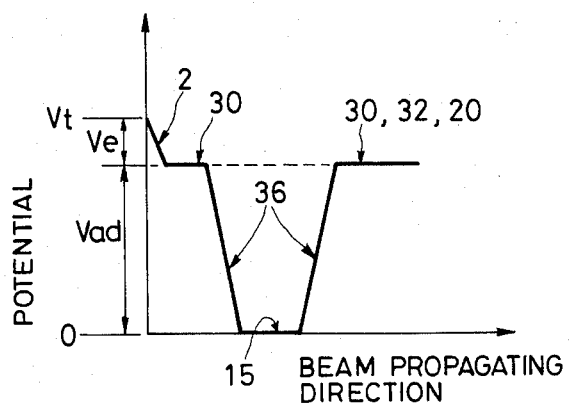
FIG. 11 is a diagram showing the potential profile of the system depicted in FIG. 10.

FIG. 11 shows the potential profile of the system according to the embodiment under discussion; sample 15 is at the point of zero potential, the deflecting magnets 30 and 32 and measuring instrument 20 being at a point equal to the accelerating/decelerating voltage Vad, the accelerating/decelerating tube 36 being at a point between the two potentials, and the ionization source 2 being at a point between Vad and $Va$ ($=Vad+Ve$).

From the same consideration as applied to derive Eq. (11), the energy E of the scattered beam 4 entering the measuring instrument 20 can be expressed as:

$$E=qVa-\Delta E-qVad=qVe-\Delta E \qquad (14)$$

and E>0 is condition to be satisfied for the system of FIG. 10 to operate Eq. (14) corresponds to Eq. (10), so that in the system under discussion the spectrum of energy loss can be determined by changing either the extraction voltage Ve or voltage $V_{ESA}$ to be imposed on the energy analyzer 21.

Figure 1:
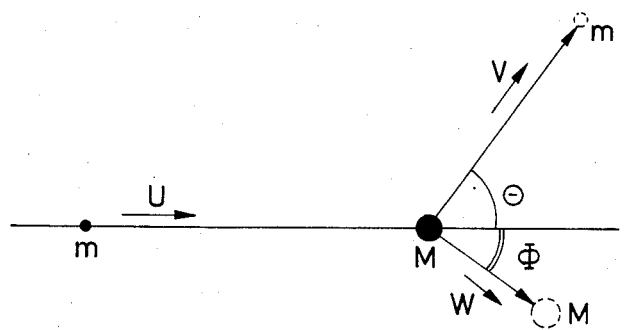
FIG. 1 is a velocity diagram both before and after collision between an atom M and a proton m; for the purpose of explaining the principle of PELS.
Figure 2:
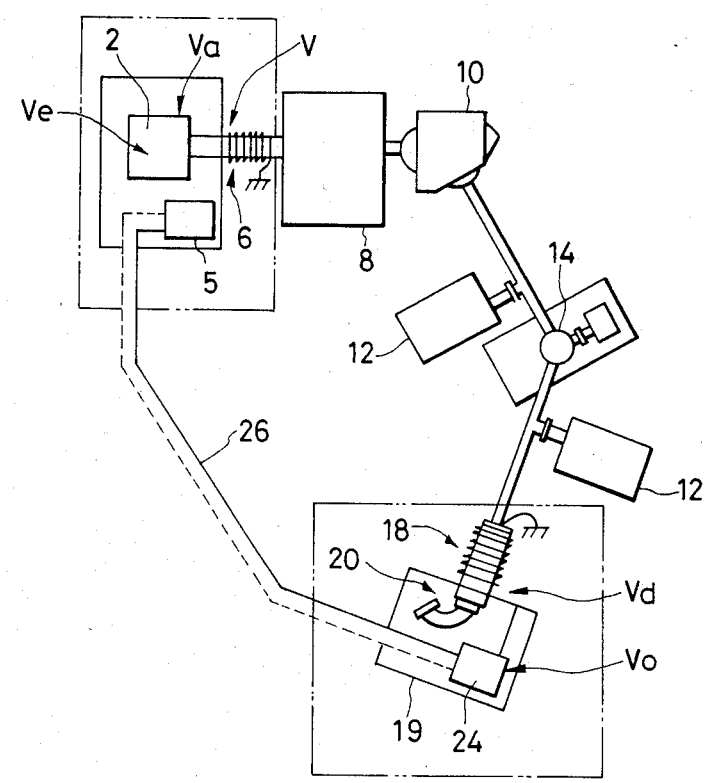
FIG. 2 is a schematic plan view of prior art surface analyzer.
Figure 3:
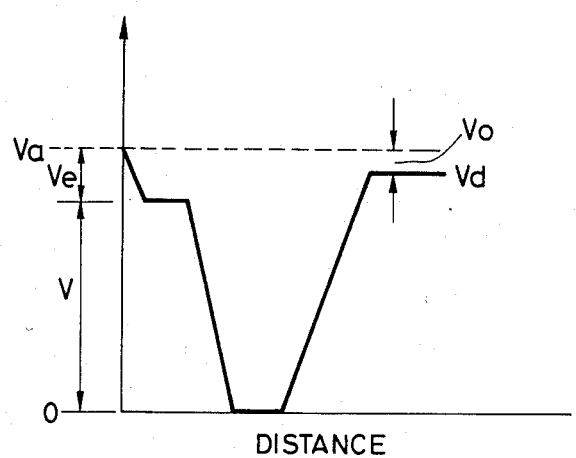
FIG. 3 is a diagram showing the potential profile of the system depicted in FIG. 2.
Figure 4:
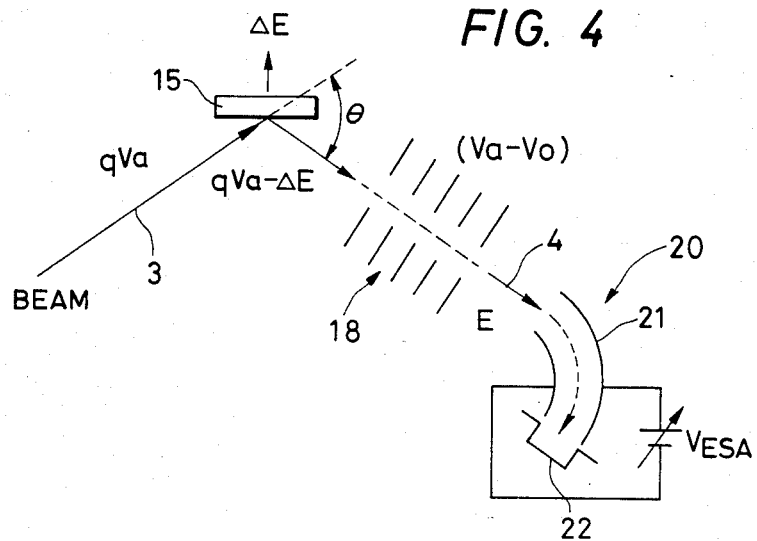
FIG. 4 is a sketch for illustrating the operating principles of the system shown in FIG. 2.

The system being discussed has the following advantages over the prior art system shown in FIG. 2.

(1) The potential profile is simplified and contains only two high-potential sectors, Va and Vad. This permits the use of a simplified electrical circuit while obviating the need to employ the heretofore required high-tension cable 26. As a result, trouble such as the disturbance of power sources by noise can be sufficiently reduced to prevent the deterioration of the performance, such as the energy resolving power, of the system.

(2) Since the system has only two high-potential sectors, it requires a smaller space for providing insulation and hence the overall size of the equipment can be reduced. In addition, the ionization source 2, allied apparatus, the measuring instrument 20 and even the deflecting magnets 30 and 32 can be mounted on a single high-potential table 38, and this is another factor that contributes to a reduced size of the equipment.

(3) The offset power source 24 used in the system of FIG. 2 is eliminated from the surface analyzer of the present embodiment. In addition, in this embodiment, the accelerating tube 6 and the decelerating tube 18 are replaced by a single accelerating/decelerating tube 36. This embodiment leads to the use of fewer components and hence a decrease in the manufacturing cost of the equipment than the first and second embodiments.

The structural relationship between the two deflecting magnets 30 and 32 is hereunder described although this is essentially the same as in the system of FIG. 6. The two deflecting magnets are designed to satisfy the following conditions:

$$\Phi_1=\Phi_2$$

$$\alpha_1=\alpha_2=(\Phi_1/2)-90 \text{ (degrees) and}$$

$$r_1=r_2$$

where $\Phi_1$ is the angle of deflection of the scattered beams in the magnet 30, $\alpha_1$ is the angle at which the scattered beams emerge from the magnet 30, $r_1$ is the radius of curvature of a scattered beam 4a with no energy loss ($\Delta E=0$), $\Phi_2$ is the angle of deflection of the scattered beams in the magnet 32, $\alpha_2$ is the angle at which the scattered beams are admitted into the magnet 32, and $r_2$ is the radius of curvature of the scattered beam 4a. In the particular embodiment under discussion, $\Phi_1=\Phi_2=90°$ and $\alpha_1=\alpha_2=-45°$ (the minus sign is generally attached to $\alpha_1$ and $\alpha_2$ in the case shown in FIG. 10).

If the three conditions noted above are satisfied, the scattered beams 4a and 4b that have been separated from a single track in the deflecting magnet 30 will travel on parallel paths as they emerge from the magnet 30 and enter the deflecting magnet 32. Therefore, using the measuring instrument 20, the quantities of scattered beams from the top few layers of the sample 15 can be measured at a time by simply tilting the sample (the angle of its inclination depends both on the sample and on the specific monolayer in which the incident beams are to be scattered) and an energy spectrum of the shape shown in FIG. 5 can be attained with high efficiency without the need to change the extraction voltage Ve or the voltage $V_{ESA}$ applied to the energy analyzer 21. This offers the additional advantage of eliminating any of the effects that may be produced as a result of changes in the energy state occurring during the course of spectrum analysis. The advantages afforded by the present embodiment are: it reduces the occurrence of troubles in power sources and thereby prevents deterioration of the system performance; the system has a smaller size and can be manufactured at a lower cost.

Figure 13:
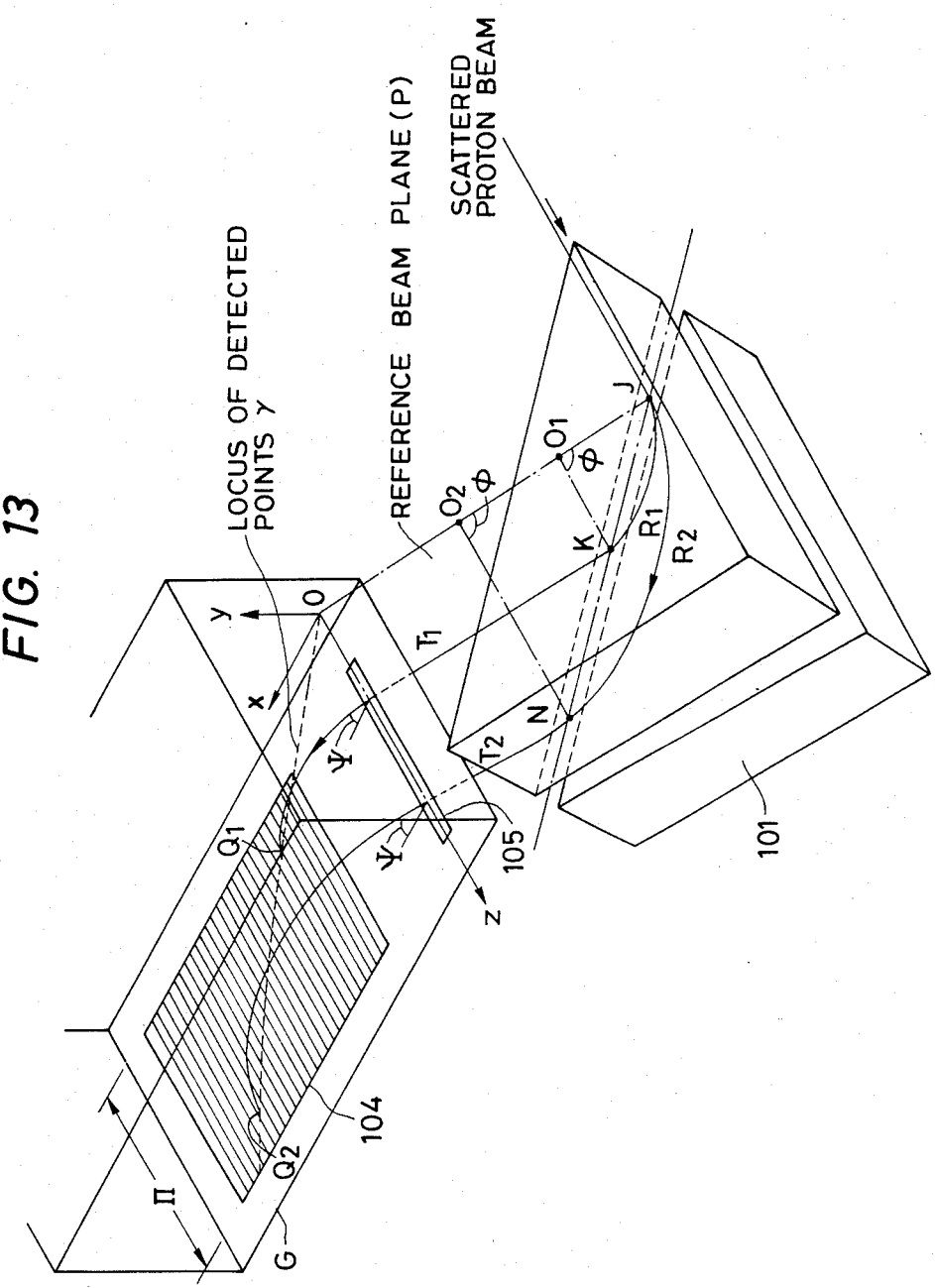
FIG. 13 is a perspective view showing the relative positions of a magnet and an analyzer according to fourth embodiment of the present invention.

In the fourth embodiment as shown in FIG. 13, only one magnet is used to bend decelerated proton beams. In the above-described embodiments, two magnets are required because it is necessary to converge proton beams at a single point.

FIG. 13 is a perspective view showing the relative positions of a magnet 101 and an analyzer G incorporating the concept of the present invention. Magnet 101 corresponds to magnet 30 in FIGS. 7 and 11. Analyzer G is wider than analyzers as shown in the other embodiments and employs the same principles of measurement. Other components of the fourth embodiment are the same as the embodiments described above, and therefore are omitted hereinafter.

To understand this embodiment more easily, assuming scattered proton beams having two levels of energy enter the magnet 101 at point J. Beams of the lower energy travel along a track $R_1$ having the smaller radius of curvature and emerge from the magnetic field at point K. Beams of the higher energy travel along a track $R_2$ having the larger radius of curvature and emerge from the magnetic field at point N. If the centers of tracks $R_1$ and $R_2$ are written as $O_1$ and $O_2$, respectively, points J, $O_1$, $O_2$, K and N are all situated in the reference beam plane (P). After leaving the magnetic field at points K and N, the two beams will travel along straight tracks $T_1$ and $T_2$, which are also included in the reference beam plane (P).

The analyzer G is positioned in such a manner that its bottom surface forms an angle $\Psi$ with respect to the reference beam plane (P) and that the slit 105 in the analyzer will traverse the reference beam plane (P).

Consider here a rectangular coordinate system in which z-axis is taken along the slit 105, y-axis dropped perpendicular to the bottom surface of the analyzer, and x-axis directed from the slit towards the position detector 104. The proton beams spread over the area $T_1$-$T_2$ but are admitted into the analyzer G through an elongated slit 5. In the analyzer G, a voltage of Vo is applied downwardly. After passing through the slit 105, the proton beams will travel in a plane that is parallel to x-y plane but because of the applied voltage Vo, they are depressed toward the bottom of the analyzer to fall into either one of the channels in the position detector 104.

The origin O of the x-y-z coordinate system is determined as the point at which the plane that passes through point J (i.e., at which the scattered beams enter the magnet 101 and which is perpendicular to the reference beam plane (P) intersects the center line of the slit 105. This is possible if the transversal width of the analyzer is sufficiently great.

Beam $T_1$ will fly over a short distance and fall at point $Q_1$ in the position detector, whereas beam $B_2$ will fly over a longer distance and fall at point $Q_2$ in the position detector. Protons of high energy will pass through the slit at a large value of z and their length of flight L in the analyzer is great. On the other hand, protons of low energy will pass through the slit at a small value of z and their length of flight L in the analyzer is small. Therefore, the points at which the protons fall in the position detector 104 will draw a curve if they are connected together, and the protons will not fall all points of the detector 104. The locus of the falling points of the protons is hereinafter referred to as the locus of detection points $\Psi$, which may be determined by the following procedures wherein the detection point is denoted by Q.

From Eq. (28), the x-coordinate of point Q is given by:

$$x = \frac{2Eah \sin(2\Psi)}{meVo} \tag{15}$$

The z-coordinate of point Q depends on the amount of deflection of a proton by magnet 1 and is given by:

$$z = R\sin\Phi \tag{16}$$

where $\Phi$ is a deflection angle such as $<KO_1J$, and R is the radius of curvature of proton bending. Since the velocity of a proton V is the product of R and the angular cyclotron frequency $\Omega c$ of the proton beam, $$\Omega cR = V \tag{17}$$

Since $$\Omega c = \frac{eH}{mc} \tag{18}$$

and $$V = \left(\frac{2Ea}{m}\right)^{\frac{1}{2}} \tag{19}$$

$$z = \frac{c}{eH} \sqrt{2mEa} \sin\phi \tag{20}$$

Eliminating Ea from Eq. (15) and (20), $$x = \frac{h\sin(2\Psi)}{eVo\, C^2\sin\phi} z^2 \tag{21}$$

Therefore, the locus $\gamma$ of point Q on the x-z plane is a parabola.

Eq. (21) contains the cyclotron frequency $\Omega c$. The proton and the ions of other atoms have different masses and hence different value of $\Omega c$. If the top surface of the position detector 104 is masked with a plate having a cutout whose contour follows the locus $\gamma$, the ions of any unwanted atoms are blocked by the mask and will not enter the position detector. Therefore, the mask is effective in preventing count errors that will otherwise occur because of the presence of unwanted ions.

The width $\pi$ of the slit 105 and the position detector 104 in z-direction depends on the expected variation in proton energy Ea and the greater this variation, the larger $\pi$ should be. The variation in proton energy Ea is closely related to the variation in the mass M of the atom to be investigated. For instance, $\pi$ of approximately 10 cm is sufficient cover a fairly wide range of masses.

The angle of deflection, $\Phi$, of protons in the magnet 101 may or may not be 90°. If $\Phi$ is 90°, it can be seen from Eq. (16) that good beam separation can be achieved in z-direction. However, it is more important to achieve good beam separation in x-direction than in z-direction. If $\Phi$ is large, the size of the magnet 101 must be increased. If $\Phi$ is small, the space in which the analyzer G can be installed is limited. From these considerations, $\Phi$ is generally selected from the range of 30°–150°, desirably within the range of from about 45° to about 135°.

The surface analyzer of the present embodiment has the following advantages:

(1) A magnet 32 as shown in FIGS. 6 and 10 is eliminated and elimination of this bulky magnet contributes to a substantial reduction in the overall size of PELS equipment;

(2) the use of a simplified high-potential table is realized;

(3) the beam line from the sample to the analyzer is shortened and this allows for reduction in the length of the accelerating/decelerating tube;

(4) the number of operational parameters is decreased to provide for a simpler operation of the equipment;

(5) high reproducibility is attained in analysis;

(6) a uniform proton transport efficiency is realized;

(7) simultaneous measurements can be achieved over a broad range of atomic masses; and (8) a mask with a cutout whose contour follows the locus of detection point may be placed over the position detector so as to prevent any of the ions other than protons from entering this detector.

The following description are some examples of methods of measuring various objects by employing the surface analyzer according to this invention.

A. Depth Analysis by Shadow Cone

Figure 14:
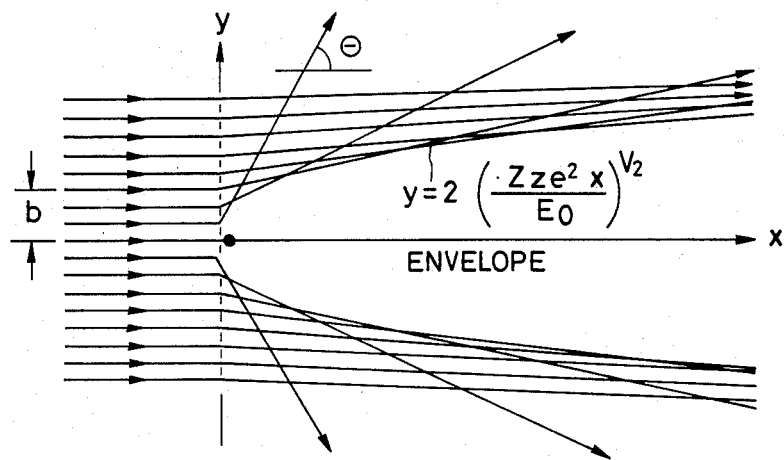
FIG. 14 shows how a shadow cone is created in the forward direction when protons are scattered by an atom.

As shown in FIG. 14, when protons having mass m are scattered by a heavy atom M, an area where no protons exist will occur in the forward direction and this is generally referred to as a shadow cone. If x-axis is drawn through the atom M parallel to motion of individual protons, a shadow cone is produced because protons far from the x-axis are scattered at small angle while those near the x-axis are scattered at large angles.

Assuming the atom with a charge Ze and a proton with a charge ze, the track of the proton undergoing Coulomb scattering is expressed by the following polar equations:

$$\frac{1}{r} = (\epsilon \cos\theta - 1)B \tag{22}$$

$$\epsilon^2 = \frac{A}{B^2} + 1 \tag{23}$$

$$A = \frac{1}{b^2} \tag{24}$$

$$B = \frac{Zze^2}{2E_0B^2} \tag{25}$$

where b is the initial distance of the proton from x-axis, and $E_0$ is the kinetic energy of the proton and is the same as what is given by Eq. (7).

Eq. (12) shows that the range of scattering angles is $2\cos^{-1} 1/\epsilon$ and, therefore, the scattering angle $\theta$ is given by:

$$\theta = \pi - 2\cos^{-1} 1/\epsilon \tag{30}$$

As the first approximation, suppose that a proton beam bent at point $y = b$ on the y-axis flies at angle $\theta$ with respect to x-axis. Then, the locus of the proton beam after scattering is given by:

$$y - b = x \tan\theta \tag{31}$$

The shape of the shadow cone is chiefly determined by proton beams that are scattered at small angles. Therefore, as the second approximation, assume that the scattering angle $\theta$ is small (vuz., b is large). Then, $$\tan\theta \simeq 2\sin\frac{\theta}{2} \simeq \frac{2B}{\sqrt{A}} \tag{32}$$

which can be rewritten as:

$$\tan\theta \simeq \frac{Zze^2}{E_0 b} \tag{33}$$

The shadow cone which is the envelope of the family of curves expressed Eq. (31) can be found by the following procedures. First, take the partial derivative of Ea. (31) with respect to b, $$-1 = -\frac{Zze^2}{E_0 b^2} x \tag{34}$$

which can be rewritten as:

$$b = \sqrt{\frac{Zze^2 x}{E_0}} \tag{35}$$

Substituting Eq. (21) in Eq. (17), $$y = 2\left(\frac{Zze^2 x}{E_0}\right)^{\frac{1}{2}} \tag{36}$$

By using the shadow cone in a dextrous manner, one can identify the atoms in the top monolayer of a sample as shown in FIGS. 15–18.

Figure 15:
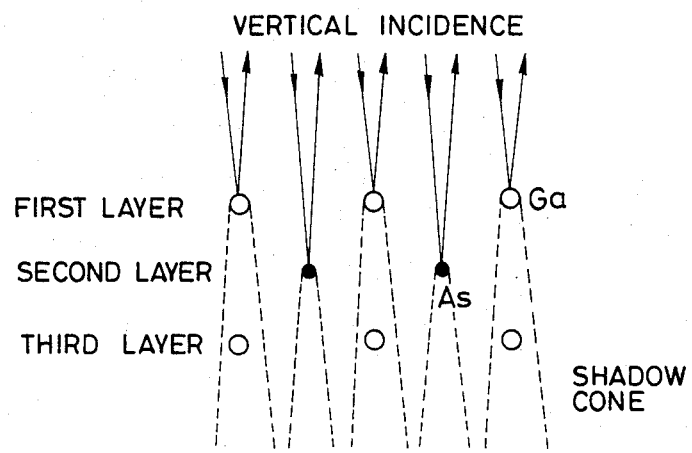
FIG. 15 is a sketch of the top few layers of a GaAs crystal showing how proton beams are incident and scattered perpendicular to the surface of the crystal in PELS.
Figure 16:
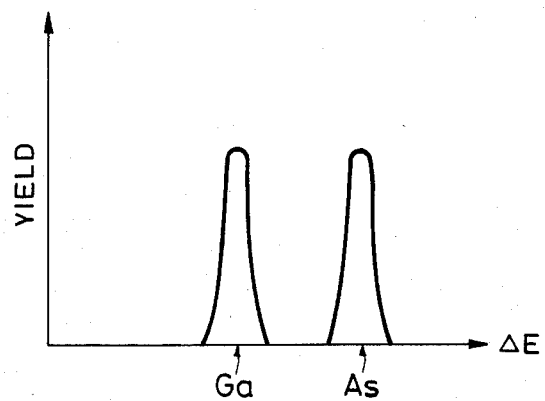
FIG. 16 is a diagram of proton energy loss that occurs in PELS when proton beams are incident in the direction indicated in FIG. 15.
Figure 17:
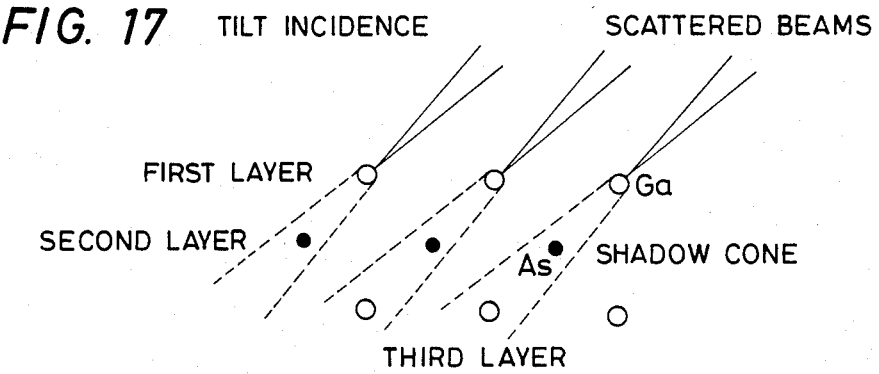
FIG. 17 is a sketch of the top two layers of a GaAs crystal showing how proton beams are incident and scattered obliquely in PELS.
Figure 18:
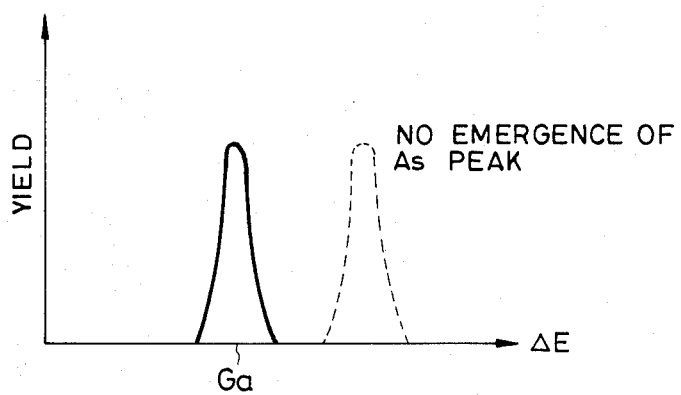
FIG. 18 is a diagram of proton energy loss that occurs in PELS when proton beams are incident in the direction indicated in FIG. 17.

Suppose proton beams are directed perpendicular to the surface of a sample as shown in FIG. 15 for measuring the energy distribution of protons reflected in opposite direction ($\theta = \pi$). The yield of scattered protons has two peaks as shown in FIG. 11. If the sample is GaAs, FIG. 16 alone is insufficient to tell whether Ga or As atoms are present in the top monolayer of the surface. If, on the other hand, proton beams are impinged on the sample at an angle as shown in FIG. 17 such that the atoms of the element in the second top layer are located within the shadow cones created by the atoms of the element in the topmost layer, the energy distribution of protons will have only one peak as shown in FIG. 18, revealing that Ga atoms are present in the topmost layer.

B. Depth Analysis Based on Collision with Electrons

PELS is also capable of differentiating atoms in the top monolayer from those in the underlying (second top) layer. PELS is a technique of analysis that identifies atoms in a sample based on the distribution of energy loss caused by collision between protons and atoms. In the sample, protons are also subjected to the effects of scattering by electrons. The mass of electrons is so small that the motion of the protons will be little impeded by electrons. However, protons as well as electrons are charged particles and will lose energy because of collision with electrons which outnumber the protons. This energy loss by protons can be used to tell in which of the top two monolayers of the sample the protons have been scattered.

Figure 19:
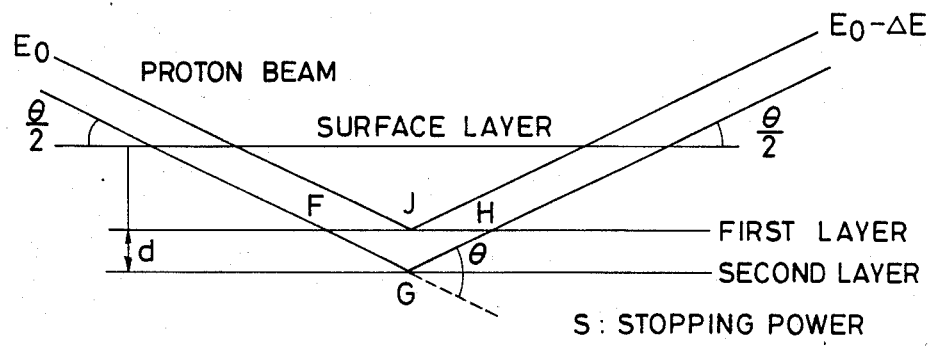
FIG. 19 is a scattering cross-sectional diagram showing how the topmost layer of a sample can be distinguished from its second top layer in terms of the increase in proton energy loss due to collision with electrons.

The details of this mechanism will be hereunder described with reference to FIG. 19. Consider two cases, one in which an incident proton is scattered at point J in the topmost layer and the other case where it is scattered at point G in the second top layer. In both cases, the proton is scattered in the direction of θ/2 which is an angle formed with respect to the plane of each layer. The scattering angle is θ but this does not mean that scattering of the proton occurs only in the direction of θ/2 according to Bragg's law. What is meant here is that although protons can be scattered in any direction, only the energy distribution of protons that have been scattered in the direction of θ/2 is measured in PELS of the present invention.

Suppose electrons have a stopping power S, which is defined as the energy lost by a proton passing through an electron-containing sample per unit length of path. The proton scattered in the second top monolayer travels along a path that is longer than the path of the proton scattered in the topmost layer, and the difference is represented by FGH in FIG. 19 which causes the former proton to be subjected to correspondingly large effects of the stopping power of electrons. If the difference in energy between the protons scattered in the topmost and second top monolayers is expressed as ΔF, $$\Delta F = 2dS\cosec\frac{\theta}{2} \quad (37)$$

If d=5.6 A, S=10 eV/A and θ=30, $$\Delta F = 432\ 1\ ev \quad (38)$$

If θ is increased, ΔF is decreased correspondingly; for example, θF=112 eV if θ=180°. In other words, if proton beams are incident perpendicular to the sample, the energies of the protons that have been scattered in the topmost and second top monolayers differ from each other by approximately 100 eV. Furthermore, by decreasing θ, ΔF can be sufficiently increased to provide for distinction between proton scatterings by dissimilar atoms in the topmost and second top monolayers.

What is claimed is:

1. A surface analyzer for analyzing physical properties of the surface of a sample, said surface analyzer comprising:
   an ion beam source of generation ion beams;
   deflecting means comprising a first deflecting magnet and second deflecting magnet, said first deflecting magnet for deflecting said ion beams from said ion beam source, to irradiate the surface of said sample with said deflected ion beams in a direction perpendicular to said surface of said sample, and for deflecting scattered ion beams form said sample to said analyzer through use of said second deflecting magnet;
   accelerating and decelerating means in line with said first and second deflecting magnets, for accelerating said ion beams before said ion beam impinge on said sample and decelerating said scattered ion beams from said sample; and
   analyzing means for detecting said scattered beams and analyzing an energy loss of said ion beams.

2. A surface analyzer for analyzing physical properties of the surface of a sample, said surface analyzer comprising:
   an ion beam source for generation ion beams;
   deflecting means comprising a first deflecting magnet and a second deflecting magnet, said first deflecting magnet for deflecting said ion beams from said ion beam source, for irradiating the surface of said sample with said deflected ion beams in a direction perpendicular to said surface of said sample, and for deflecting scattered ion beams from said sample to said analyzer through use of said second deflecting magnet;
   accelerating an decelerating means in line with said first and second deflecting magnets for accelerating said ion beams before said ion beams impinge on said sample and decelerting said ion beams from said sample; and
   analyzing means for detecting said scattered ion beams and analyzing an energy loss of said ion beams;
   wherein said first deflecting magnet is disposed between said ion beam source and said sample for deflecting said ion beam prior to impingement thereof on said sample and for deflecting said scattered ion beams from said sample, and said second deflecting magnet being disposed between said sample and said analyzing means for deflecting said scattered ion beams from said sample to said analyzing means.

3. The surface analyzer as claimed in claim 2, wherein said second deflecting magnet is positioned so as to deflect as scattered ion beams from said sample in the same direction as said first deflecting magnet.

4. The surface analyzer as claimed in claim 3, wherein said accelerating and decelerating means comprises accelerating means and decelerating means, said accelerating means being disposed between said ion beam source and said first deflecting magnet for accelerating said ion beams from said ion beam source and said decelerating means being located between said second deflecting magnet and said analyzing means for decelerating said scattered ion beams from said second deflecting magnet.

5. The surface analyzer as claimed in claim 3, wherein said accelerating and decelerating means is located between said first deflecting magnet and said sample for both accelerating said ion beams from said first deflecting magnet and decelerating said scattered ion beams from said sample.

6. The surface analyzer as claimed claims 4 or 5, wherein said first and second deflecting magnets are designed so as to satisfy the following equation, $\Phi_1 = \Phi_1$, $\alpha_1 = \alpha_2 = (\Phi_1/2) - 90$ (degrees), and $r_1 = r_2$, where $\Phi_1$ is the angle of deflection of said scattered ion beams in said first deflecting magnet, $\alpha_1$ is the angle at which said scattered ion beams emerge from said first deflecting magnet, $r_1$ is the radius of curvature of a scattered ion beam with no energy loss in said first deflecting magnet, $\Phi_2$ is the angle of deflection of said scattered ion beams in said second deflecting magnet, $\alpha_2$ is the angle at which said scattered beam with no energy loss is admitted into said second deflecting magnet, and $r_2$ is the radius of curvature of a scattered beam with no energy loss in the second deflecting magnet.

7. A surface analyzer for analyzing physical properties of a surface of a sample, said surface analyzer comprising:
   an ion beam source for generating ion beams;
   deflecting means comprising a plurality of deflecting magnets for deflecting said ion beams from said ion beam source, for irradiating the surface of said sample with said deflected ion beams in a direction perpendicular to said surface of said sample, and for deflecting scattered ion beams from said sample to said analyzer;

accelerating and decelerating means in line with said plurality of deflecting magnets for accelerating said ion beams before said ion beams impinge on said sample and decelerating said scattered ion beams from said sample; and analyzing means for detecting said scattered ion beams and analyzing an energy loss of said ion beams;

wherein said plurality of deflecting magnets are disposed between said sample and said analyzing means for deflecting said scattered ion beams from said sample and leading to said analyzing means with said scattered ion beams being parallel to one another on the same plane.

8. The surface analyzer as claimed in claim 7, wherein said analyzing means comprises an elongated slit for passing therethrough said parallel ion beams and a broad position detector for detecting said parallel ion beams passed through said slit.

9. The surface analyzer as claimed in claim 8, wherein said plurality of deflecting magnets included a first deflecting magnet designed in such a manner that said scattered ion beams enter said first deflecting magnet at a first point and emerge from said first deflecting magnet at a plurality of second points, said first point and said plurality of second points lying on the same straight line, and wherein a reference beam plane comprises said parallel ion beams from first deflecting magnet formed of said scattered ion beams pass through said slit while said parallel ion beams intersect said slit at right angles.

10. The surface analyzer as claimed in claim 9, wherein said analyzing means further comprises a mask having a cutout whose contour follows the focus of predetermined ion beams to be detected in said position detector, said mask being placed over said position detector to prevent ion beams other than said predetermined ion beams from being detected by said position detector.

11. The surface analyzer as claimed in claim 7, wherein said deflecting magnets are positioned so as to deflect said scattered ion beams within the range from 45° to 135°.

12. The surface analyzer as claimed in claim 7, wherein said ion beam source comprises a source of proton beams.

* * * * *

UNITED STATES PATENT AND TRADEMARK OFFICE
CERTIFICATE OF CORRECTION

PATENT NO. : 4,829,179

DATED : May 9, 1989

INVENTOR(S) : Masahiko Aoki et al.

It is certified that error appears in the above-identified patent and that said Letters Patent is hereby corrected as shown below:

Claim 1, column 17, line 45, change "of generation" to --for generating--.

Claim 1, column 17, line 57, change "beam" to --beams--.

Claim 10, column 20, line 11, change "focus" to --locus--.

Signed and Sealed this

Twenty-first Day of August, 1990

Attest:

HARRY F. MANBECK, JR.

*Attesting Officer*     *Commissioner of Patents and Trademarks*